US00PP34673P2

(12) United States Plant Patent
Elsworth

(10) Patent No.: US PP34,673 P2
(45) Date of Patent: Oct. 18, 2022

(54) ***AJUGA* PLANT NAMED 'CORCAN'**

(50) Latin Name: ***Ajuga reptans* x *Ajuga tenorii***
Varietal Denomination: 'Corcan'

(71) Applicant: Kelly Elsworth, Portage, MI (US)

(72) Inventor: Kelly Elsworth, Portage, MI (US)

(73) Assignee: Christopher M. Hansen, Zeeland, MI (US)

( * ) Notice: Subject to any disclaimer, the term of this patent is extended or adjusted under 35 U.S.C. 154(b) by 0 days.

(21) Appl. No.: 17/687,232

(22) Filed: Mar. 4, 2022

(30) Foreign Application Priority Data

Dec. 22, 2021 (QZ) ..... 20213428

(51) Int. Cl.
*A01H 6/00* (2018.01)
*A01H 5/02* (2018.01)

(52) U.S. Cl.
USPC ..... Plt./401

(58) Field of Classification Search
USPC ..... Plt./401
CPC ..... A01H 6/00; A01H 5/02
See application file for complete search history.

*Primary Examiner* — Keith O. Robinson
(74) *Attorney, Agent, or Firm* — Penny J. Aguirre

(57) ABSTRACT

A new cultivar of *Ajuga* plant named 'Corcan' that is characterized by its unique vibrant yellow colored foliage, its leaves that are very small in size, its vigorous growth habit, its cobalt blue flowers that bloom in late spring, and its stem internodes that are pink in color when young and green-yellow in color when they mature.

2 Drawing Sheets

Botanical classification: *Ajuga reptans* x *Ajuga tenorii*.
Variety denomination: 'Corcan'.

CROSS-REFERENCE TO RELATED APPLICATIONS

This application claims priority to European Community Plant Variety Office (CPVO) Plant Breeder's Rights Application No. 2021/3428 filed on Dec. 22, 2021, under 35 U.S.C. 119(f), the entire contents of which is incorporated by reference herein. This application is co-pending with a U.S. Plant Patent Application filed for a plant derived from the same breeding program that is entitled *Ajuga* Plant Named 'Fanfin' (U.S. Plant patent application Ser. No. 17/687,273).

BACKGROUND OF THE INVENTION

The present invention relates to a new and distinct cultivar of *Ajuga* of hybrid origin and will be referred to hereafter by its cultivar name, 'Corcan'. 'Corcan' represents a new cultivar of *Ajuga*, an herbaceous perennial grown for landscape use.

The new Invention arose from an ongoing controlled breeding program in Hudsonville, Mich. The objective of the breeding program is to develop new cultivars of *Ajugas* with unique foliage coloration, different leaf sizes and strong clump forming growth habits.

The new cultivar arose from a controlled cross made by in Inventor in March of 2019 between an unnamed and unpatented plant of *Ajuga reptans* with gold foliage as the female parent and *Ajuga tenorii* 'Chocolate Chip' (not patented) as the male parent. The Inventor selected 'Corcan' as a single unique plant from amongst the seedlings of the above cross in May of 2020.

Asexual propagation of the new cultivar was first accomplished by stem tip cuttings in June of 2020 in Hudsonville, Mich. Propagation by stem tip cuttings and division has determined the characteristics to be stable and reproduced true to type in successive generations.

SUMMARY OF THE INVENTION

The following traits have been repeatedly observed and are determined to be the characteristics of the new cultivar. These attributes in combination distinguish 'Corcan' as a unique cultivar of *Ajuga*.

1. 'Corcan' exhibits unique vibrant yellow colored foliage.
2. 'Corcan' exhibits leaves that are very small in size.
3. 'Corcan' exhibits a vigorous growth habit.
4. 'Corcan' exhibits cobalt blue flowers that bloom in late spring.
5. 'Corcan' exhibits stem internodes that are pink in color when young and green-yellow in color when they mature.
6. 'Corcan' exhibits a high resistance to sun scorch and thrives in full sun in the summer in Michigan.

The female parent plant of 'Corcan' differs from 'Corcan' in having leaves that are much larger in size, flowers that are pink in color, and a larger plant size. The male parent plant of 'Corcan' differs from 'Corcan' in having foliage that is purple in color. 'Corcan' can be most closely compared to *Ajuga tenorii* cultivar 'Mint Chip' (U.S. Plant Pat. No. 20,734) and *Ajuga* 'Fanfin'. 'Mint Chip' is similar to 'Corcan' in having flowers that are blue in color and a similar leaf shape and size. 'Mint Chip' differs from 'Corcan' in having foliage and stem internodes that are green in color. 'Fanfin' is similar to 'Corcan' in having flowers that are blue in color, foliage with some yellow color and in being a cold hardy groundcover. 'Fanfin' differs from 'Corcan' in having foliage colors that are a mixture of yellow, apricot and burgundy and in producing more flowers.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but are not limited to website publications by Jung Seed, Growing Colors, Garden Solutions Plants, Sugar Creek Gardens, Great Garden Plants, Pahls, Plant Delights, Wilson Bros Gardens, Gateway Gardens, In the Country Garden and Gifts, White House Perennials, Winter Green House, Bloomin Designs, Faller Landscape, Garden Center Point, Mountain Crest Gardens Blue Sky Nursery, Roots Rhizomes, Floral Acres, Garden Center Ohio, Mary Snoddy, Campbells Nursery, Libellules Creations, Garden, Quality Cuttings, Pinterest, Blue Sky Nursery, Shop Bedners, Emerisa, Plant Central, Rideau Woodland Ramble, Masty Young Plants, George Weigel, Honeymoon Acres, Terra Nova Nurseries, Green Profit, Bot Garden, Rotary Botanical Gardens, Amsterdam Green Houses, Germania Seed, Greenland Garden, Preen, Evergreen Nursery Inc, Sticks and Stones Garden, You Tube, Phoenix Neo Codes of Software, Peconic River Herb Farm, Groffs Plant Farm, Bakers Acres Greenhouse, Shopewdell, Plant Care Today, Pleasant Run Nursery, North Shore Plant Club, Bill Moore Co, SVGPlants, Christensen Plant Center, Right Plant Place, Intrinsic Perennial Gardens, Facebook, IRP-CDN-Multiscreensite, ehrnet, Zyromski, Etsy, Sherwood-Forests, ifcs, Fairfax County, Be Strong Physio, and Decommunicacio.

BRIEF DESCRIPTION OF THE DRAWINGS

The accompanying color photographs illustrate the overall appearance and distinct characteristics of a 2-year-old plant of the new *Ajuga* as grown in a greenhouse in a 1-gallon container in Hudsonville, Mich.

The photograph in FIG. 1 provides a top view of 'Corcan' in bloom.

Figure 1:
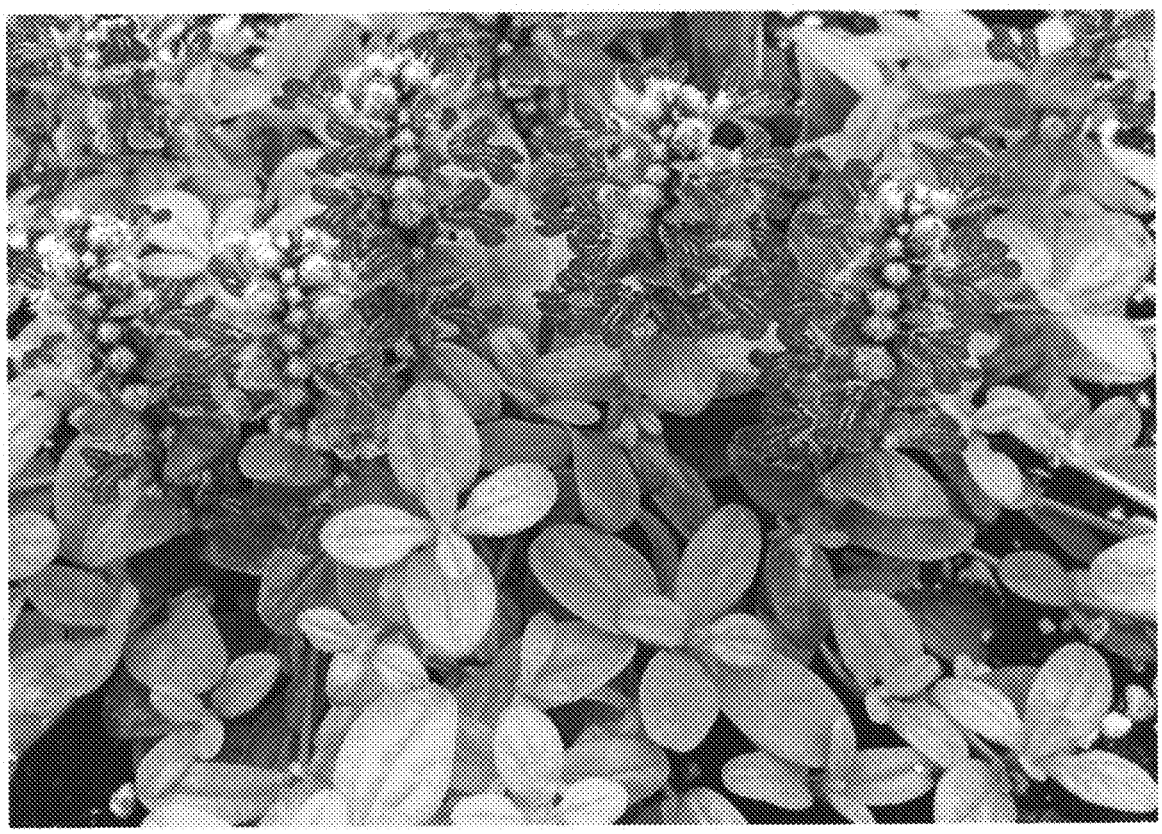
Figure 2:
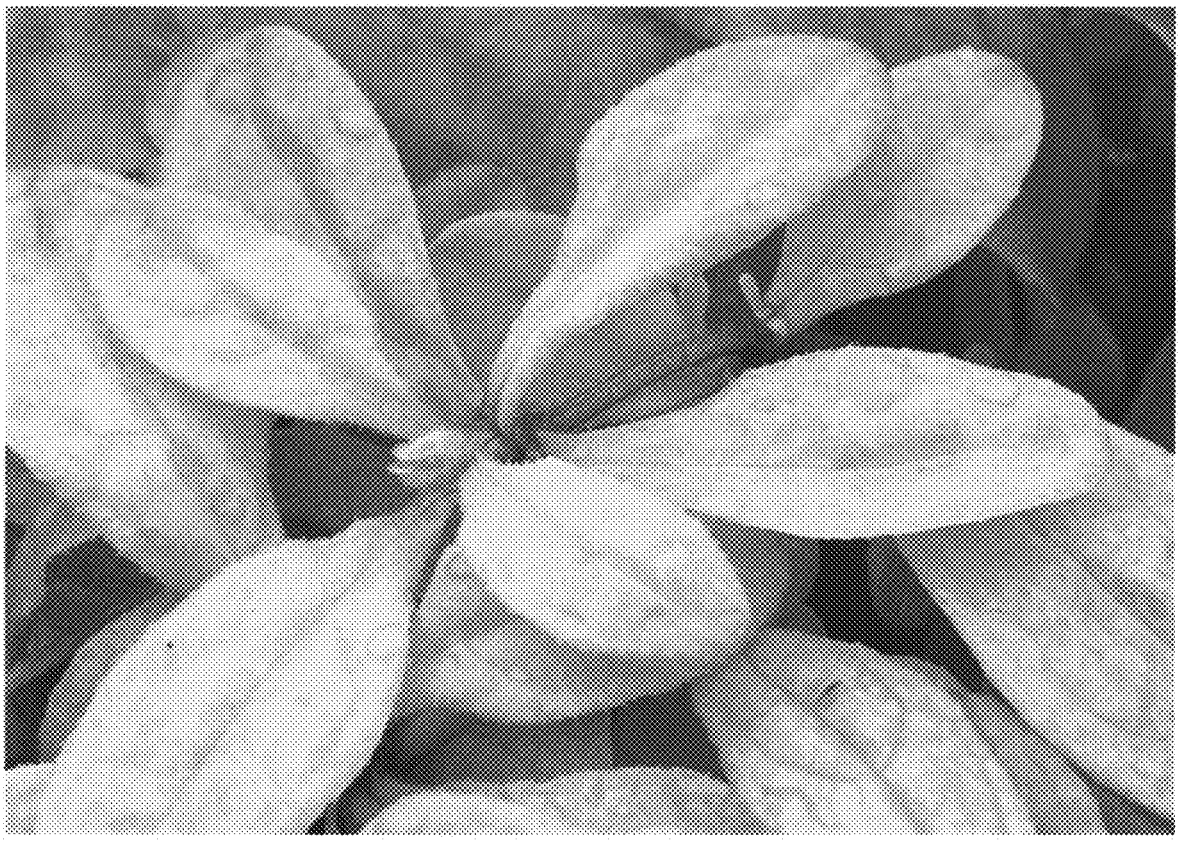

The photograph in FIG. 2 illustrates a close-up view of the foliage of 'Corcan'.

The colors in the photographs may differ slightly from the color values cited in the detailed botanical description, which accurately describe the colors of the new *Ajuga*.

DETAILED BOTANICAL DESCRIPTION

The following is a detailed description of 6-month-old plants of the new *Ajuga* as grown in 4-inch containers in a greenhouse in Hudsonville, Mich. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

*Blooming period.*—4 to 6 weeks in late spring into summer in Michigan.

*Plant type.*—Herbaceous perennial.

*Plant habit.*—Dense and rounded, groundcover, compact upright inflorescences.

*Height and spread.*—7 cm in height (soil level to top of floral plane), an average of 5 cm in height (soil level to top of foliar plane) and 9 cm in width, a mature plant in the landscape reaches an average of 10 cm in height and 46 cm in spread.

*Cold hardiness.*—At least in U.S.D.A. Zones 4 to 8.

*Diseases and pests.*—Plants have been observed to be disease free, however no resistance to any specific diseases is known, no resistance or susceptibility to pests has been observed.

*Root description.*—Fine and fibrous, a blend of 158A and NN155A in color.

*Propagation type.*—Stem cuttings and division.

*Root development.*—An unrooted stem cutting will fully root in a 50-cell plug in 8 weeks and a 50-cell plug will fully root in a 1-gallon container in 10 weeks.

*Growth rate.*—Vigorous.

*Branching habit.*—Basal rosettes of leaves from rhizomes.

Foliage description:

*Leaf shape.*—Spatulate.

*Leaf division.*—Simple.

*Leaf base.*—Truncate to base of rhizome.

*Leaf apex.*—Rounded.

*Leaf venation.*—Pinnate, matches surface colors.

*Leaf margins.*—Entire to slightly undulate.

*Leaf attachment and arrangement.*—Whorled, held in in clumps.

*Leaf orientation.*—Mostly upright.

*Leaf surface.*—Very finely puberulent, matte on upper surface, slightly rough to the touch, lower surface smooth, glabrous, slightly glossy.

*Leaf color.*—Young and mature upper and lower surface; a blend of 145A and 147B.

*Leaf size.*—Average of 3.5 cm in length, 1 cm in width.

*Leaf quantity.*—Average of 30 in a clump 1.5 cm in diameter.

*Leaf attachment.*—Sessile.

Flower description:

*Inflorescence type.*—Verticillaster, terminal spike, individual flowers in clusters held in leaf-axils.

*Inflorescence size.*—An average of 5 cm in height and 2.5 cm in width.

*Inflorescence number.*—50 to 70 blooms as a fully mature plant grown in a 1-gallon container.

*Lastingness of inflorescence.*—10 to 14 days, self-cleaning.

*Flower type.*—Labiate.

*Flower number.*—Average of 25 per inflorescence.

*Flower fragrance.*—None.

*Flower buds.*—Oblanceolate to rounded in shape, average of 2 mm in length and 1.75 mm in diameter, color; 145B, at bud burst 92B, immature calyx 145B, surface is matte and very densely covered with soft woolly pubescence; up to 1 mm in length, NN155D in color.

*Flower size.*—Average of 1 cm in depth, 5 mm in diameter, throat 2 mm in diameter, tube 5 mm in length and 1.5 mm in diameter.

*Peduncles.*—An average of 4 cm in length, 2 mm in diameter, quadrangular, vertical angle to slightly nodding, moderately strong, color; 183A, surface is glossy and sparsely covered with very short hairs; 1 mm in length, NN155D in color.

*Calyx.*—Rotate and tubular in shape, 2 mm in length and diameter.

*Sepals.*—5, 50% fused at base, average of 1 mm in length, 0.5 mm in width, ovate in shape, apex acute, entire margins, surface is covered with long woolly hairs matching surface color, color inner and outer surface 145A.

*Petals.*—50% of petals fused into tube, upper central lobe; notched, average of 5 mm in length, 3 mm in width, blunt and rounded in shape, obtuse apex, entire margins, no undulation, upper and lower surface glabrous, matte, color; upper surface when opening and fully open inner section between veins 92B, veins, margins and apex 93A and 93B, lower surface when opening and fully open 93D, outer lobes; 6, average of 3 mm in length, 1 mm in width, oblanceolate in shape, apex is obtuse, entire margins, slight undulation, upper and lower surface glabrous and slightly glossy, velvety, color; upper surface when opening and fully open inner section between veins 92B, veins, margins and apex 93A and 93B, lower surface when opening and fully open 93D, flower throat; outer surface covered with woolly soft pubescence, inner surface is smooth and glabrous, color; inner and outer surface when opening and fully open 93B, flower tube; inner and outer surfaces glabrous, color inner and outer surfaces when opening and fully open 93B.

Reproductive organs:

*Pistils.*—1, style; 6 mm in length, 92D in color, base NN155D in color, stigma; non-distinguishable, ovary; oblong, 2 mm in length, 1 mm in width, NN155D in color.

*Stamens.*—6, filament; implanted into flower tube, average of 4.5 mm in length, 97C in color, anthers; club-shaped, 0.5 mm in diameter, 203A in color, pollen; moderate and 17A in color.

*Fruit.*—Fruit and seed production has not been observed to date.

It is claimed:

1. A new and distinct variety of *Ajuga* plant named 'Corcan' as described and illustrated herein.

* * * * *